(12) United States Patent
Niznick (10) Patent No.: US 9,456,881 B1
(45) Date of Patent: Oct. 4, 2016

(54) DENTAL ATTACHMENT ASSEMBLY

(76) Inventor: Gerald A. Niznick, Las Vegas, NV (US)

( * ) Notice: Subject to any disclaimer, the term of this patent is extended or adjusted under 35 U.S.C. 154(b) by 953 days.

(21) Appl. No.: 12/925,022

(22) Filed: Oct. 12, 2010

Related U.S. Application Data (63) Continuation-in-part of application No. 12/798,658, filed on Apr. 7, 2010, now abandoned.

(51) Int. Cl.
*A61C 8/00* (2006.01)

(52) U.S. Cl.
CPC .............. *A61C 8/0053* (2013.01); *A61C 8/005* (2013.01); *A61C 8/0062* (2013.01); *A61C 8/0075* (2013.01); *A61C 8/0048* (2013.01); *A61C 8/0086* (2013.01)

(58) Field of Classification Search
CPC .............. A61C 8/0048–8/0078; A61C 8/0086
USPC ........ 433/172–178, 181–182, 191, 193–194, 433/201.1; 623/17.17
See application file for complete search history.

(56) References Cited

U.S. PATENT DOCUMENTS

| | | | | |
|---|---|---|---|---|
| 4,540,367 A * | 9/1985 | Sulc | ............................... | 433/181 |
| 5,120,222 A * | 6/1992 | Sulc | ............................... | 433/181 |
| 5,195,891 A * | 3/1993 | Sulc | ............................... | 433/173 |
| 5,556,280 A * | 9/1996 | Pelak | ............................ | 433/172 |
| 6,030,219 A * | 2/2000 | Zuest et al. | .................... | 433/181 |
| 6,299,447 B1* | 10/2001 | Zuest et al. | .................... | 433/172 |
| 2006/0183078 A1* | 8/2006 | Niznick | ........................ | 433/173 |
| 2009/0155745 A1* | 6/2009 | Laux | ............................. | 433/174 |
| 2010/0055645 A1* | 3/2010 | Mullaly et al. | ............... | 433/174 |
| 2010/0285426 A1* | 11/2010 | Nardi | ............................ | 433/173 |

* cited by examiner

*Primary Examiner* — Edward Moran
(74) *Attorney, Agent, or Firm* — Patrick Bright (57) ABSTRACT

A dental attachment assembly has an abutment portion at the proximal end of a one-piece dental implant (an "abutment portion"), or is an abutment for attachment to a dental implant or to a bar joining two or more dental implants, and a two-part assembly including a metal cap for placement in/attachment to a dental appliance. The cap includes a flanged skirt that projects from the top surface of the cap. A second part, a plastic insert, snaps firmly inside the cap.

15 Claims, 11 Drawing Sheets

DENTAL ATTACHMENT ASSEMBLY

This application is a continuation-in-part of U.S. patent application Ser. No. 12/798,658, filed on Apr. 7, 2010 now abandoned. I hereby incorporate by reference the entire text and drawings of that application as though set forth here in full.

BACKGROUND OF THE INVENTION

This invention relates to dental attachment or anchoring structures for attaching dental appliances such as overdentures, partial dentures, and the like to an endosseous dental implant, or to the abutment portion of a one-piece, endosseous dental implant.

In use, a wearer may experience difficulty in properly locating the female socket of an abutment portion or abutment, so that the mating, retentive end or head of the male part may hit the edge of the female part when the wearer inserts the denture. Repeated impacts of this type may damage the retentive head of the male part, reducing or losing the retention force required for proper operation of the attachment.

SUMMARY OF THE INVENTION

It is an object of this invention to provide a new and improved dental attachment assembly for securing a dental appliance with a range of vertical and/or rotational movements between the appliance and an abutment/abutment portion, allowing function while minimizing stress on the abutment/abutment portion.

A dental abutment assembly for releasable attachment of a dental appliance, comprises an abutment member that may be an abutment or abutment portion, such as an abutment for attachment to an implant or bar joining two or more implants, and a variety of attachment assemblies that provide different ranges of vertical and rotational movement of the appliance in function. The abutment member includes a female socket projecting downwards inside the abutment member from its proximal end into a retentive chamber within the abutment member, and an outer surface having a rounded portion projecting outwardly and downwardly from the upper end, providing a retentive undercut below the rounded projection. This outer surface portion is positioned in a patient's mouth to project above the tissue level.

One attachment assembly comprises a first part, namely, a metal cap secured in a dental appliance on one end. The cap includes a female housing for firm snap engagement with a second part, a plastic insert that includes, on its distal end, a male retention member. The male retention member and the female socket in the abutment member are designed for releasable snap engagement with one another, allowing for both rotational and vertical movement of the male retention member within the female socket of the abutment member. The skirt of the plastic insert projects beyond the distal border of the metal cap and the male retentive member projects beyond the distal border of the plastic skirt, such that the male retentive member passes through a narrow opening in the female socket in the abutment member as the plastic skirt engages proximal shoulder of the abutment member. Under vertical load, the male retentive member can move deeper into the female socket as the plastic skirt of the male retentive member flexes. Under lateral load, the male retentive member can rotate within the female socket, and the plastic insert's skirt can flex and rotate on the shoulder of the abutment.

A second attachment assembly comprises a first part, namely, a metal cap, secured in a dental appliance on one end, having a skirt with an inner, concave surface, and an upper internal flange projecting outwardly above the concave surface, and a second part, namely, a plastic insert with a skirt that snaps into the concave surface of the metal cap, engaging the cap's internal flange for non-rotational engagement, or a plastic insert with a skirt that snaps into the cap's concave surface, and does not engage the internal flange, allowing rotational movement between the metal cap and the plastic insert. Both plastic inserts provide retentive engagement and rotational movement over the rounded projection at the top of the abutment member. The skirt of the metal cap projects beyond the distal border of the skirt of either plastic insert. Neither assembly provides for vertical movement of the appliance in function.

The insert also has a flanged skirt that projects from the top of the insert, and a male retention member that projects from the center of the insert's bottom surface. A small space between the cap's skirt and the insert's skirt allows for lateral flexing of the insert's skirt within the metal cap's skirt. The male retention member and a female socket in the proximal end of the abutment/abutment portion are designed for releasable snap engagement with one another, allowing for both rotational and vertical movement of the male retention member within the female socket in the abutment/abutment portion. The skirt of the insert projects beyond the distal end of the skirt on the cap, and the male retention member projects beyond the distal end of the insert's skirt. The retention member may pass through a narrow opening inside the abutment/abutment portion as the insert's skirt engages the proximal shoulder of the abutment/abutment portion. Under vertical load, the male retention member can move deeper into the socket as the insert's plastic skirt flexes on the shoulder of the abutment/abutment portion, providing shock absorption. Under lateral load, the male retention member may rotate in the female socket as the insert's skirt flexes and rotates on the shoulder of the abutment/abutment portion.

Other embodiments of the dental attachment assemblies of this invention may include a one-piece implant that includes, at its proximal end, an abutment portion, and, at its upper end, a socket projecting inwardly from the upper end. The abutment portion's outer surface projects downwardly from the upper end, with the outer surface portion being positioned to project above tissue level when the implant is placed in a patient's mouth.

Still other embodiments may include an abutment for attachment to a dental implant, or to a bar. Such an abutment may have an upper end that includes an inwardly-projecting socket, and an outer surface portion projecting downwardly from the upper end. The outer surface portion projects above the tissue level in a patient's mouth when the abutment is secured in an implant or on a bar. These embodiments include a two-part male member for attachment to the abutment comprising a first part, namely, a metal cap including a first skirt with an inner, substantially cylindrical surface, and an upper internal flange projecting inwardly above the inner, substantially cylindrical surface, and a second part, namely, a plastic insert with a second skirt that snaps into the substantially cylindrical surface, and with an external flange that engages the cap's internal flange for non-rotational engagement.

The first skirt may have a substantially cylindrical external surface, and a plurality of substantially concentric, outwardly- and downwardly-projecting flanges on the substantially cylindrical external surface. This first skirt may also have an inwardly-beveled inferior edge.

The plastic insert may have a substantially flat top surface, with its external flange formed by the top of the plastic insert and a circumferential groove contiguous to, and distal to the plastic insert's top. This groove forms part of the second skirt. The external surface of the second skirt may include a first substantially cylindrical portion of sufficient size and shape to engage the inner surface of the first skirt when the plastic insert is fitted into the metal cap. The external surface of the second skirt may also include a second substantially cylindrical portion spaced from the inner surface of the first skirt when the plastic insert is fitted into the metal cap. The inner surface of the second skirt may include a substantially concave surface portion, and a distal, contiguous cylindrical portion. The substantially concave surface portion may have a size and shape sufficient to engage the outer, rounded surface near the top of an abutment/abutment portion. The second substantially cylindrical portion flexes outwardly when the plastic insert passes over such an outer, rounded surface.

The distal, contiguous cylindrical portion may have an internally-projecting bevel at its inferior edge, and the inferior edge of the first skirt preferably projects beyond the inferior edge of the second skirt.

In some embodiments, the outer locating surface portion of the abutment may have formations such as a pair of diametrically opposed notches for engagement with an insertion tool for engaging the abutment with an implant. A weep hole may connect the socket to the outside of the abutment for allowing saliva to escape and reducing hydraulic pressure resulting from inserting the attachment in the socket.

The abutment may form an angle to the axis of an implant when placed in the implant. An angled abutment has a lower, connecting portion for securing the abutment to an implant, the lower portion having a first axis, and an upper portion in which the socket is located, the socket having a second axis at an angle to the first axis. Abutment members at various angles may be provided.

BRIEF DESCRIPTION OF THE DRAWINGS

This invention may be better understood from the following description of some exemplary embodiments of the invention, taken in conjunction with the accompanying drawings in which like reference numerals refer to like parts and in which:

FIGS. 2 A-B and 3 A-B are perspective views of exemplary alternatives of the abutments shown in FIGS. 1A-1D;

DETAILED DESCRIPTION OF THE DRAWINGS

FIGS. 1A-1D show abutment 10 having a distally-threaded external, cylindrically-shaped region 13. Abutment 10 includes proximal, round shouldered portion 40, with proximal opening 46 into internal passage or shaft 44. Shaft 44 includes lead-in bevel 43 surrounded by flat upper surface 41. Surface 41 includes rounded shoulder 23. Inside shaft 44 are proximal opening 46, inwardly-projecting flange 47 with flat bottom surface 15, then internal region 14.

Two-part attachment member 20 includes a first part, namely, a plastic insert 32 and a second part, namely, a metallic cap 31. Insert 32 has a flat upper surface 26 connected to outwardly, downwardly projecting flange 51, and with substantially cylindrical skirt 21 connect to flange 51. At the bottom, on the interior edge of skirt 21, is inwardly-beveled surface 53a which rests on, and moves over shoulder 23 of abutment 10. Cylindrically-shaped retention member 24 is connected to the center region of the bottom surface 39 of insert 32, and projects downwardly to distal flange 25.

Second part, cap 31, includes substantially flat upper surface 27 atop cylindrically-shaped region 22. Region 22 is connected to outwardly-flaring flange 28. Flange 28 is connected to distal, cylindrically-shaped skirt 29. Skirt 29 lies alongside skirt 21, with skirt 21 projecting beyond the bottom edge of skirt 29. Cap 31 firmly, releasably snap fits over insert 32 with the bottom surface 53 of flange 51 sitting on flat shoulder surface 52 inside flange 28. A small gap 60 between the external surface of insert 32 and the external surface of cap 31 allows flexing of skirt 21 on the shoulder 23 of abutment 10.

Figure 1A:
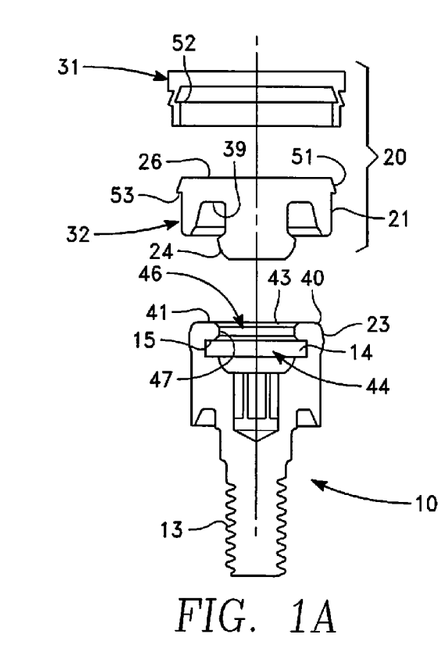
FIGS. 1A-1D are side elevation views, in vertical cross section, of a dental abutment for connection to an endosseous dental implant, and a two-part attachment assembly snap fit into, and rotatably attached to the abutment.
Figure 1B:
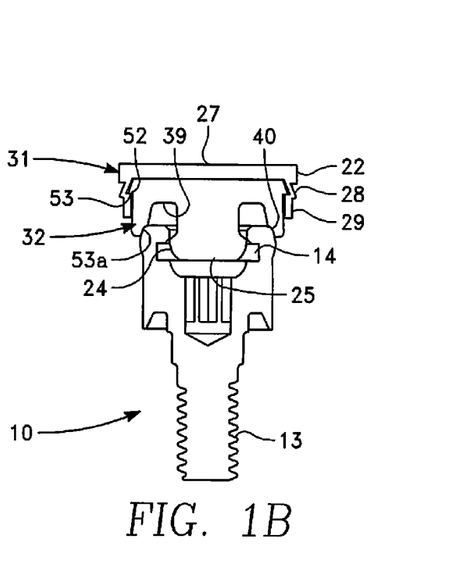
Figure 1C:
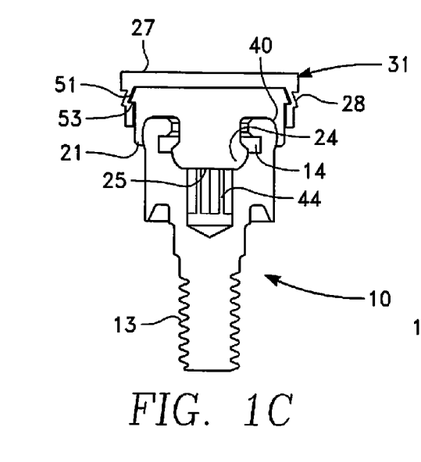
Figure 1D:
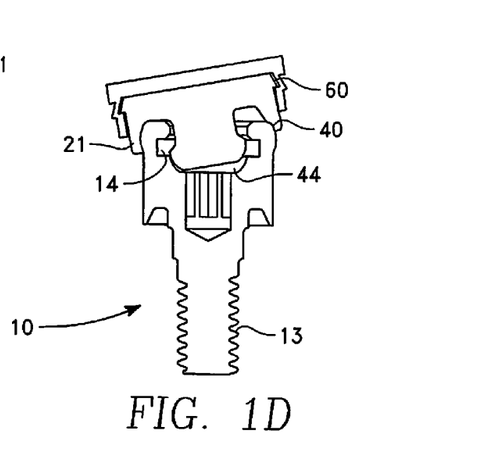

In use, cap 31 is securely seated in/attached to a dental appliance, and retention member 24/25 is releasably, rotatably inserted into region 14 with flange 25 snap fit below surface 15. Flange 25 is free to rotate along surface 15 while surface 23 rotates along surface 53, and is free to move deeper inside abutment portion 40 under vertical load, with skirt 21 flexing to move over shoulder 23, as FIG. 1C shows. Under lateral load, retention member 24/25 may rotate within portion 40 as skirt 21 rotates on shoulder 23, as FIG. 1D shows.

Figure 2A:
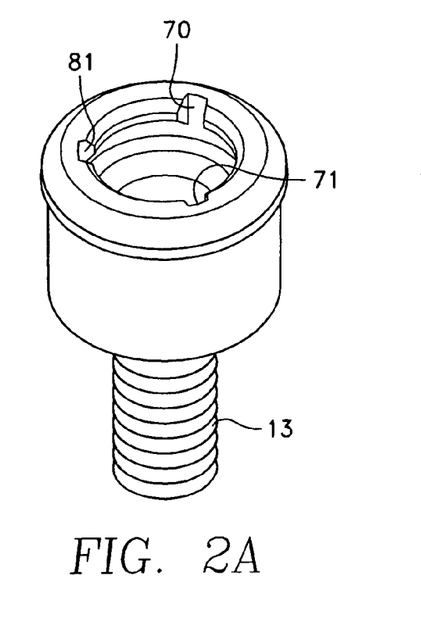
Figure 2B:
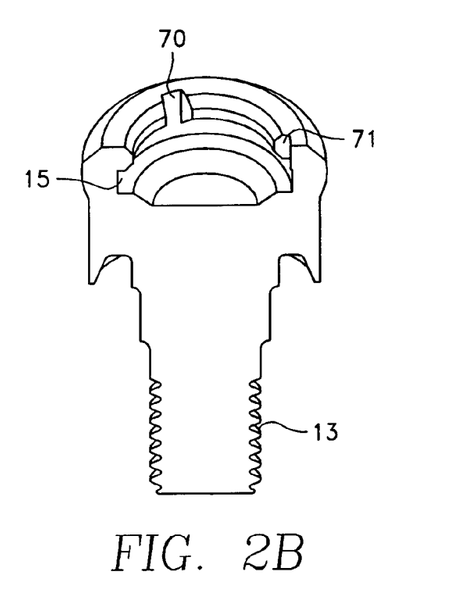
Figure 3A:
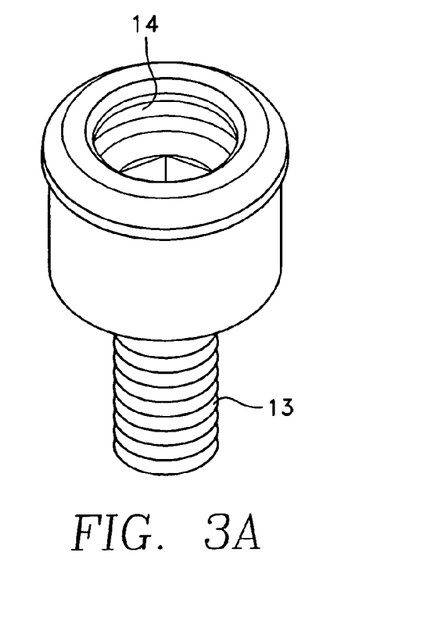
Figure 3B:
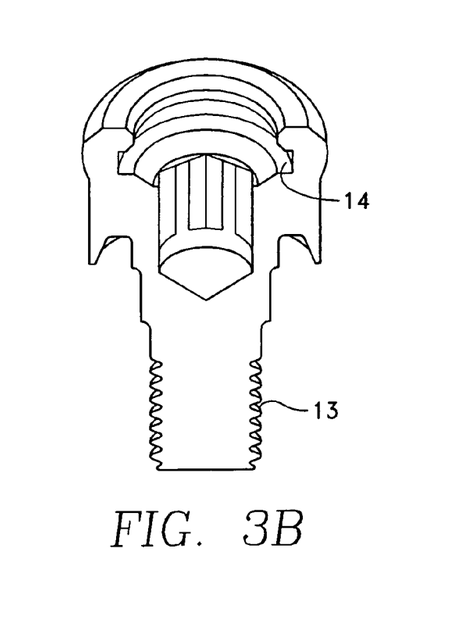

FIGS. 2A-B and 3A-B show two alternative structures for abutment 10. In FIGS. 2A-B (perspective and cross-sectional views), abutment 10 includes three proximal notches 70, 71 and 72 for engaging an insertion/rotation tool for placement of abutment 10 in the internal passage of an endosseous dental implant. In FIGS. 3A-B (perspective and cross-sectional views), abutment 10 does not include these notches, but is otherwise structurally the same as shown in FIGS. 2A-B.

Figure 4A:
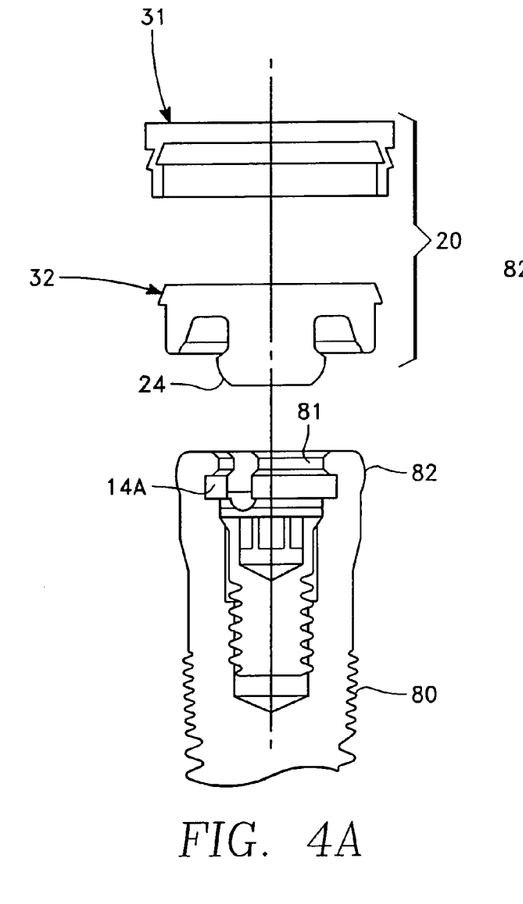
FIGS. 4A and 4B show side elevation views, in vertical cross-section, of the two-part attachment assembly of FIGS. 1A-1D snap fit into, and rotatably attached to the abutment portion of a one-piece endosseous dental implant.
Figure 4B:
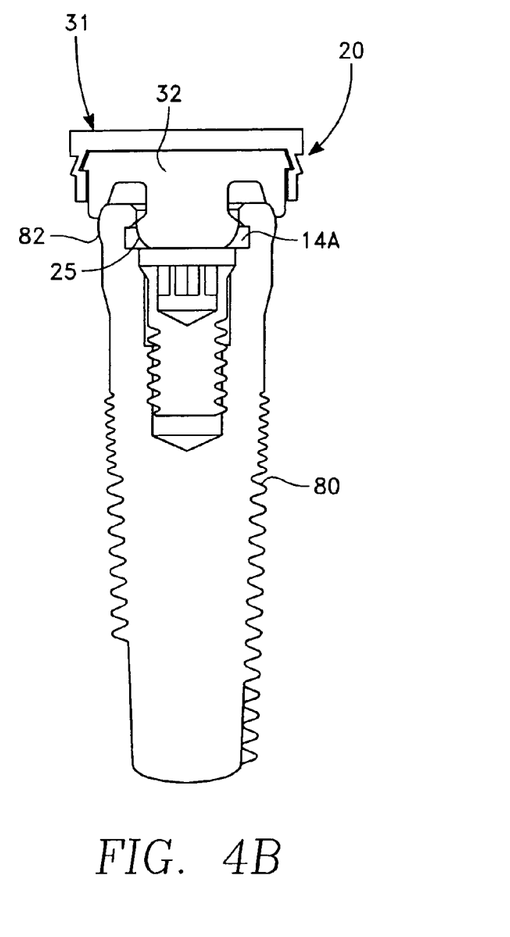

FIGS. 4A and 4B show attachment assembly 20, and its two parts, cap 31 and plastic insert 32, positioned above one-piece endosseous dental implant 80 (FIG. 4A) and connected to abutment portion 82 of implant 80 (FIG. 4B). As in FIGS. 1A-1D, retention head 24/25 snap fits into passage 14A of implant 80, allowing vertical and rotational movement of head 24/25 and of assembly 20 in passage 14A.

Figure 5A:
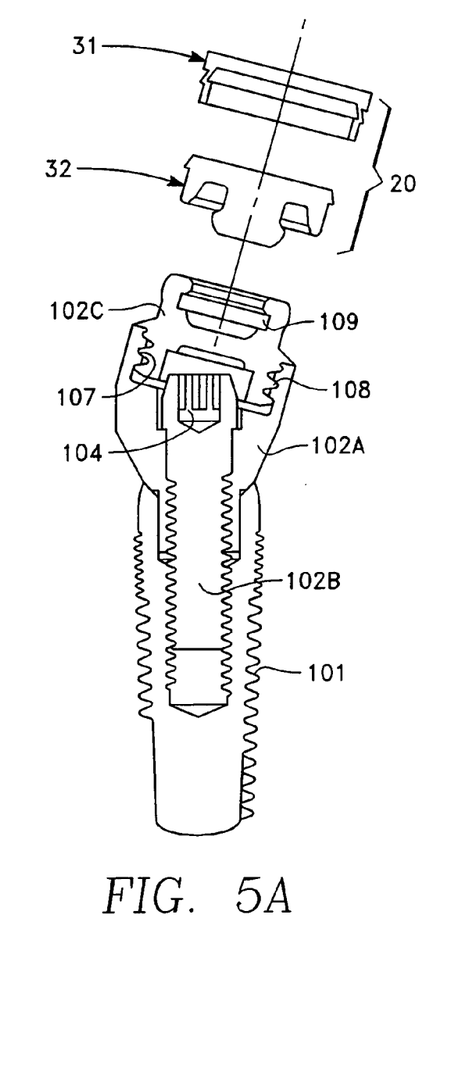
FIGS. 5A and 5B show side elevation views, in vertical cross-section, of the two-part attachment assembly of FIGS. 1A-1D snap fit into, and rotatably attached to the abutment portion of an endosseous dental implant connected to a three-part abutment.
Figure 5B:
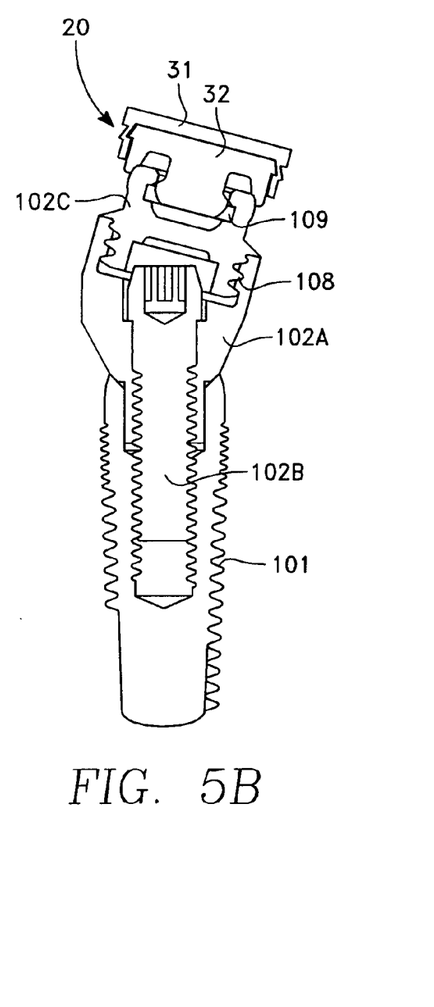

FIGS. 5A and 5B show endosseous dental implant 101, separate, three-part angled abutment 102, and attachment assembly 20 connected to, and functioning with abutment 102 as does attachment 20 with abutment portion 40 in FIGS. 1-2. Three-part angled abutment 102 includes first, angled member 102A inserted into internal passage 105 of implant 101, and held in place by threaded screw 102B. Angled abutment head 102A includes external, distal threads 107 that are screw threaded into internal, proximal threads 108 inside angled member 102A. Attachment 20 snap fits into proximal opening 109 in abutment portion 102C.

Figure 6:
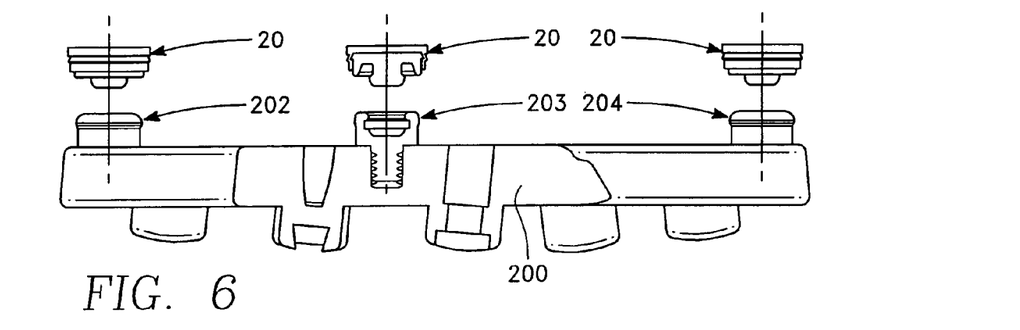
FIGS. 6-8 show side elevation views of a dental bar connected to a plurality of abutments, with each abutment snap fit connected to the two-part attachment assembly shown in FIGS. 1A-1D.
Figure 7:
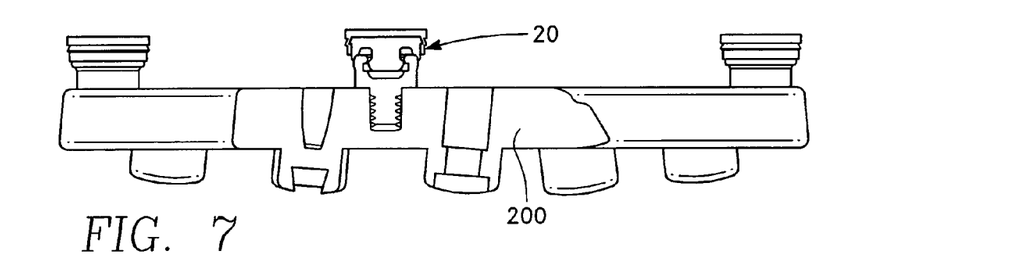
Figure 8:
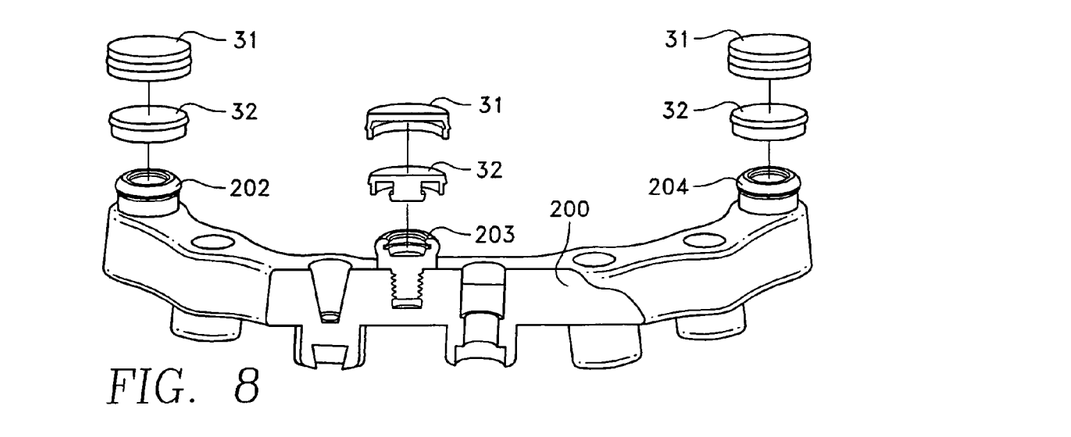

FIGS. 6-8 show denture bar 200 connected to abutments 202, 203 and 204. Attachment assemblies 20 are snap connected to each of these abutments, and function with these abutments as does attachment 20 with abutment 40 in FIGS. 1-2.

The denture or appliance can be removed repeatedly for cleaning, simply by snapping retention member 24/25 out of region 14, or by separating the first and second parts from one another, and then re-connecting them. On re-connection, skirt 21 and retention member 24/25 facilitate proper alignment.

Figure 9A:
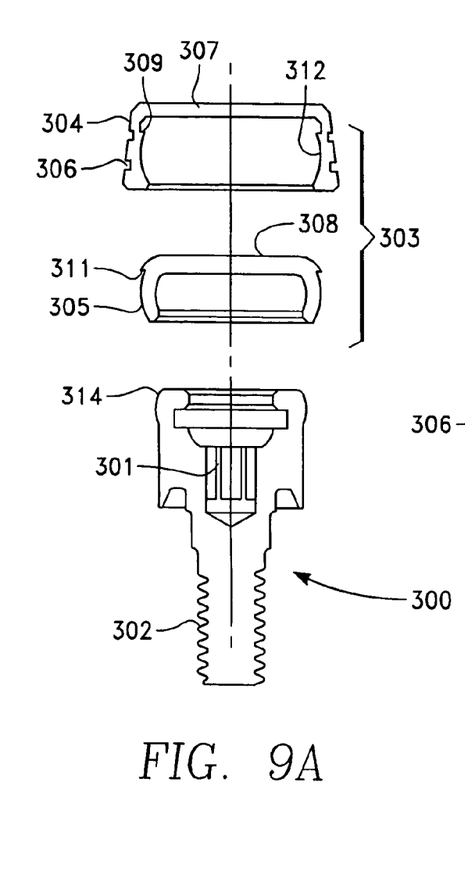
FIGS. 9A-9C show side elevation views, in vertical cross-section, of an abutment connected to a two part attachment assembly that includes a metal cap with a concave-shaped internal surface and an internal flange, and a plastic insert with a complementary external convex surface and complementary external flange for non-rotational, snap-fit engagement with one another.
Figure 9B:
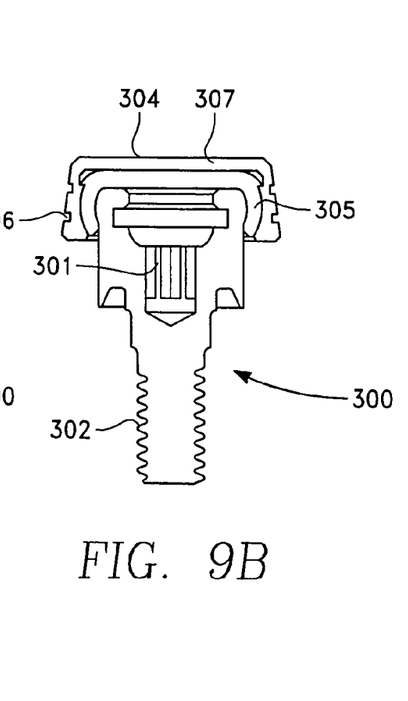
Figure 9C:
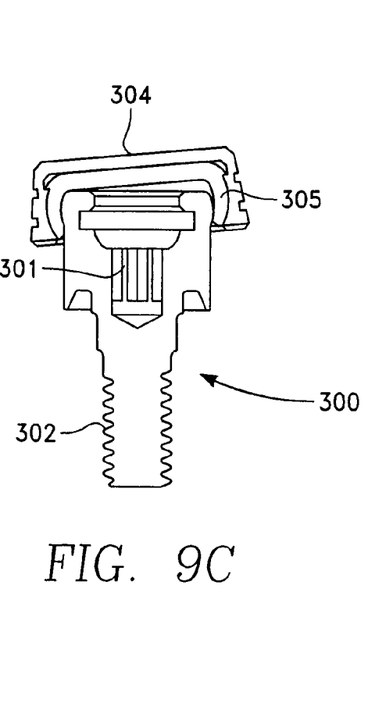

FIGS. 9A-9C show elevation views of abutment 300 in vertical cross-section with attachment assembly 303 snap fit over proximal, rounded shoulder 314 of abutment 300. Abutment 300 includes externally threaded shank 302, and internal passage 301. Assembly 303 includes metal cap 304 non-rotatably snap fit over plastic insert 305. Cap 304 includes substantially flat upper surface 307 and, projecting from surface 307, skirt 306 with internal, concave-shaped surface 312. Near the top of surface 312 is inwardly-projecting flange 309. Plastic insert 305 includes substantially flat top surface 308 and, projecting from surface 308, convex shaped skirt 311. Skirt 311 includes, near the junction of top surface 308 and skirt 311, externally-projecting flange 315. Skirt 306 projects beyond the distal end of skirt 311. When cap 304 is snap fit over insert 305, flange 315 snap fits into flange 309, precluding rotation of cap 304 and insert 305 with respect to one another. However, assembly 303 can rotate and tilt (see FIG. 9C) on rounded shoulder 314 of abutment 300.

Figure 10A:
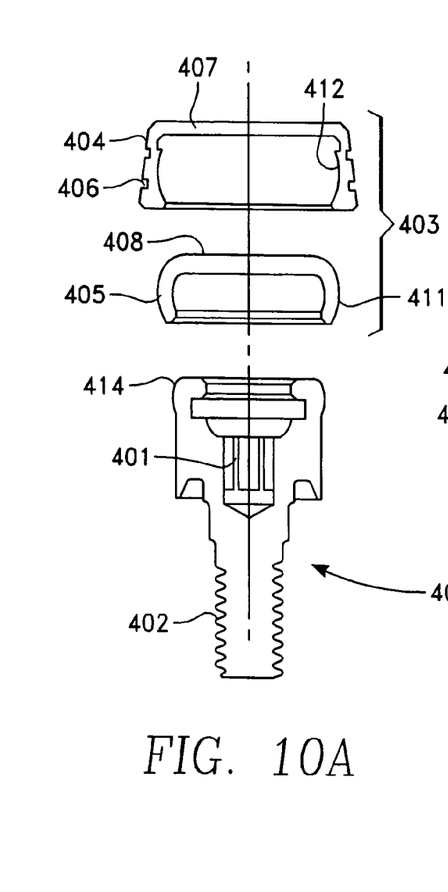
FIGS. 10A-10C show side elevation views, in vertical cross-section, of an abutment connected to a two part attachment assembly that includes a metal cap with an internal concave surface, and a plastic insert with a complementary external convex surface for rotational, snap-fit engagement with one another.
Figure 10B:
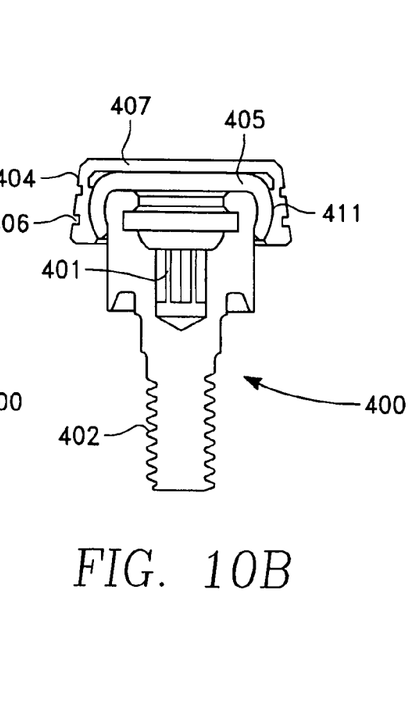
Figure 10C:
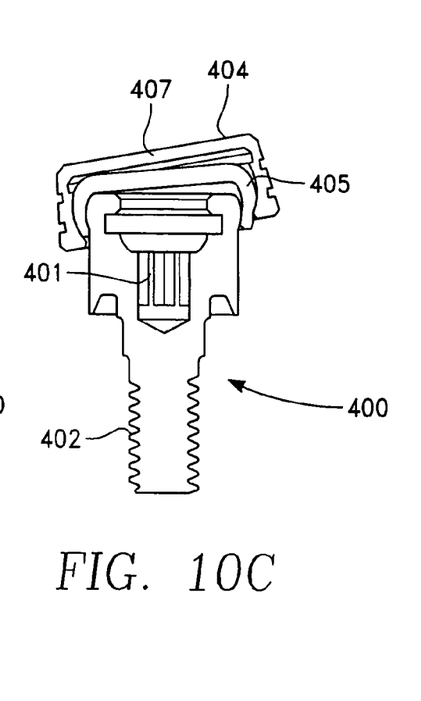

FIGS. 10A-10C show elevation views of abutment 400 in vertical cross-section with attachment assembly 403 snap fit over proximal, rounded shoulder 414 of abutment 400. Abutment 400 includes externally threaded shank 402, and internal passage 401. Assembly 403 includes metal cap 404 rotatably snap fit over plastic insert 405. Cap 404 includes substantially flat upper surface 407 and, projecting from surface 407, skirt 406 with internal, concave-shaped surface 412. Plastic insert 405 includes substantially flat top surface 408 and, projecting from surface 408, convex shaped skirt 411. Skirt 406 projects beyond the distal end of skirt 411 (see FIG. 10b). When cap 404 is snap fit over insert 405 (see FIG. 10 B), cap 404 and insert 405 may rotate or tilt (see FIG. 10C) with respect to one another, and assembly 403 can rotate on rounded shoulder 414.

Figure 11:
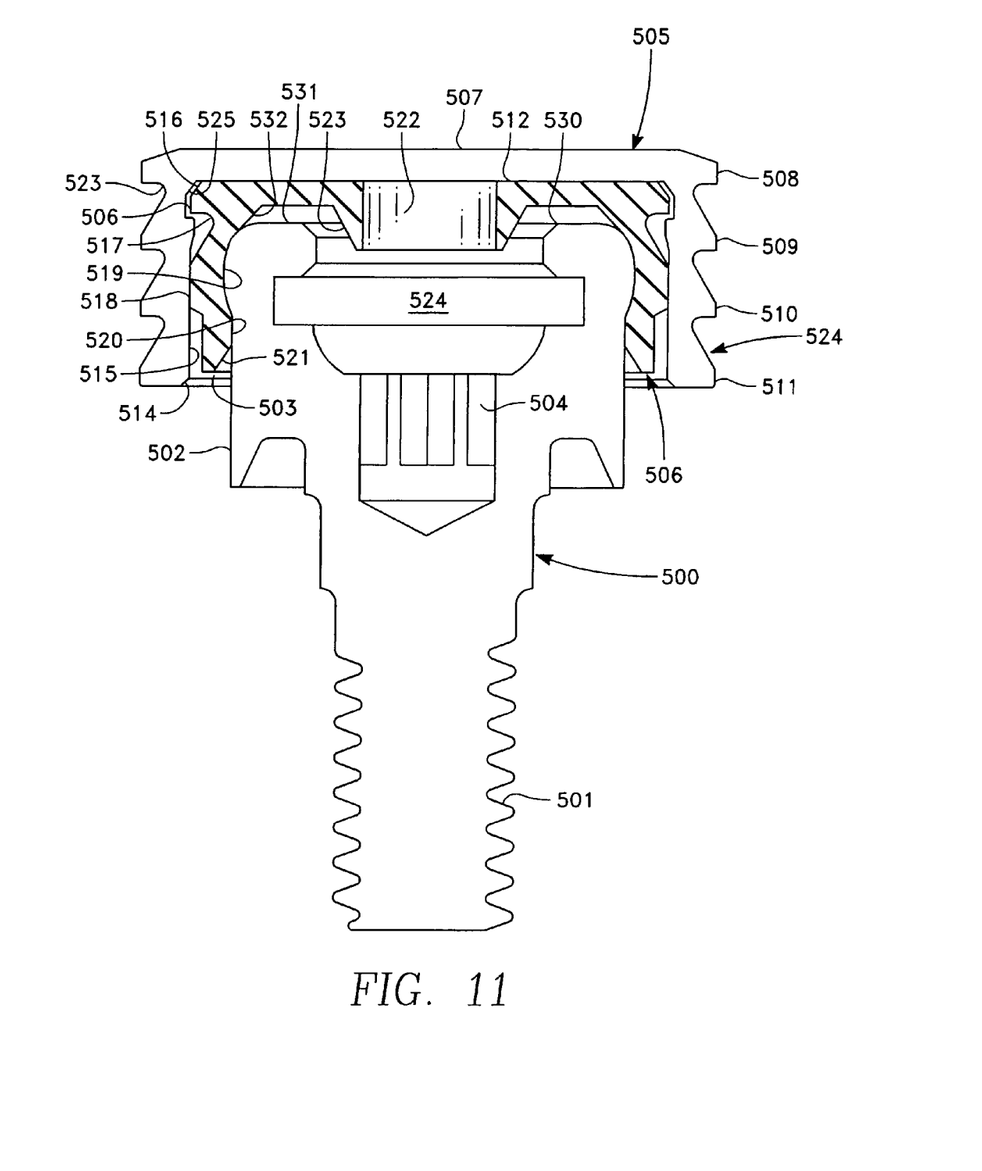
FIGS. 11 and 12 show two side elevation views, in vertical cross section, of a dental abutment for connection to an endosseous dental implant, and a two-part attachment assembly snap fit into, and non-rotatably attached to the abutment.
Figure 12:
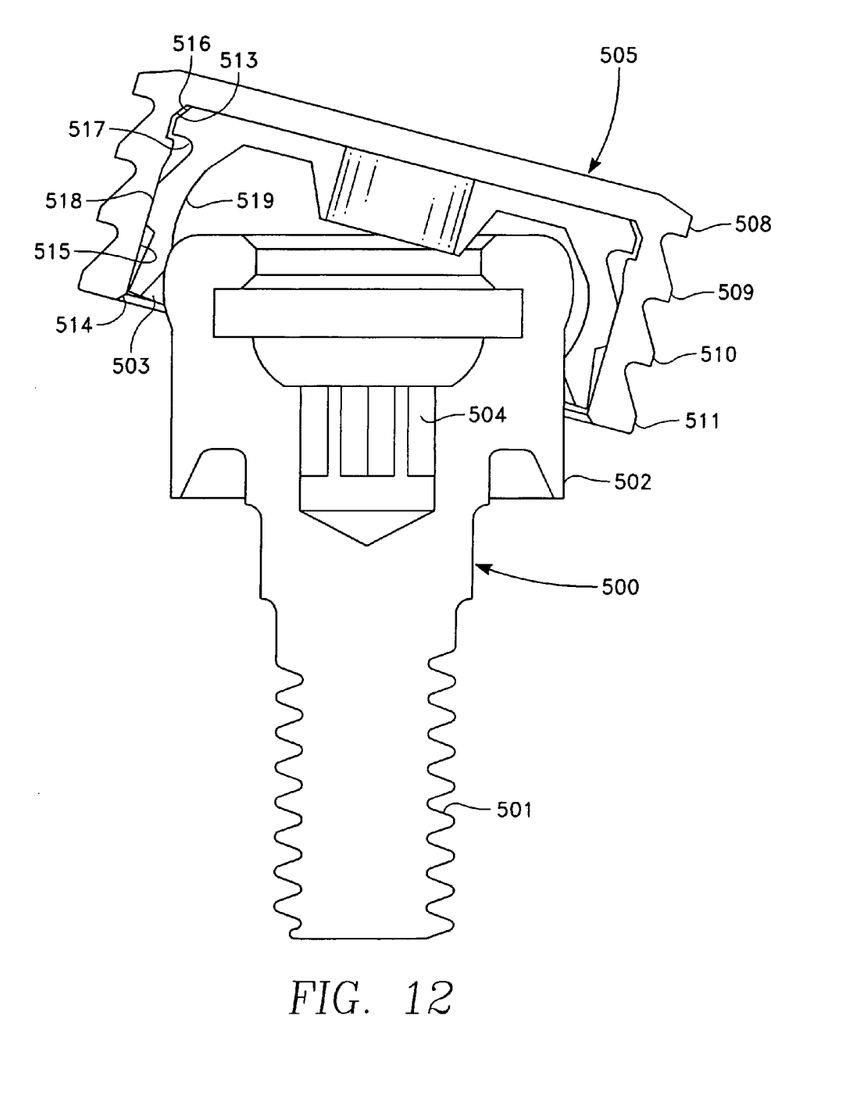

FIGS. 11 and 12 show abutment 500 that includes threaded shank portion 501 and proximal head portion 502 with outer, rounded upper surface 503. Abutment 500 also includes internal passage 504. Metal cap 505 includes flat upper, or proximal surface 507, external flange 508 extending outwardly from surface 507, and concentric, circumferential flanges 509, 510, and 511 on the external surface of first skirt 524. The inner surface 515 of first skirt 524 is substantially cylindrical, and includes inwardly projecting circumferential bevel 514 at its inferior edge, and inwardly-projecting flange 513 at its proximal end.

Plastic insert 506 snap fits inside metal cap 505, with flange 516 formed at the edge of top surface 512 extending over, and non-rotatably engaging flange 513. Flange 516 is formed by top surface 512 and groove 517. Flange 516 includes a beveled end portion 525, and a contiguous cylindrical end portion 526. Distal to groove 517 is substantially cylindrical second skirt portion 518, which is of sufficient size and shape to engage the inner surface 515 of first skirt 524. Cylindrical skirt portion 520 is contiguous to, and distal to portion 518. Portion 520 is spaced from inner surface 515, and is therefore free to flex outwardly when insert 506 passes over abutment surface 503. Concave inner surface 519 of insert 506 is of sufficient size and shape to engage the surface 503, leaving gap 530 between the upper surface 532 of abutment 500, and inner surface 531 formed under top surface 512.

Insert 506 includes central, cylindrical opening 522, and inwardly projecting portion 523, which seats in opening 524 to internal passage 504. This seating centers insert 506 on abutment 500.

Figure 13A:
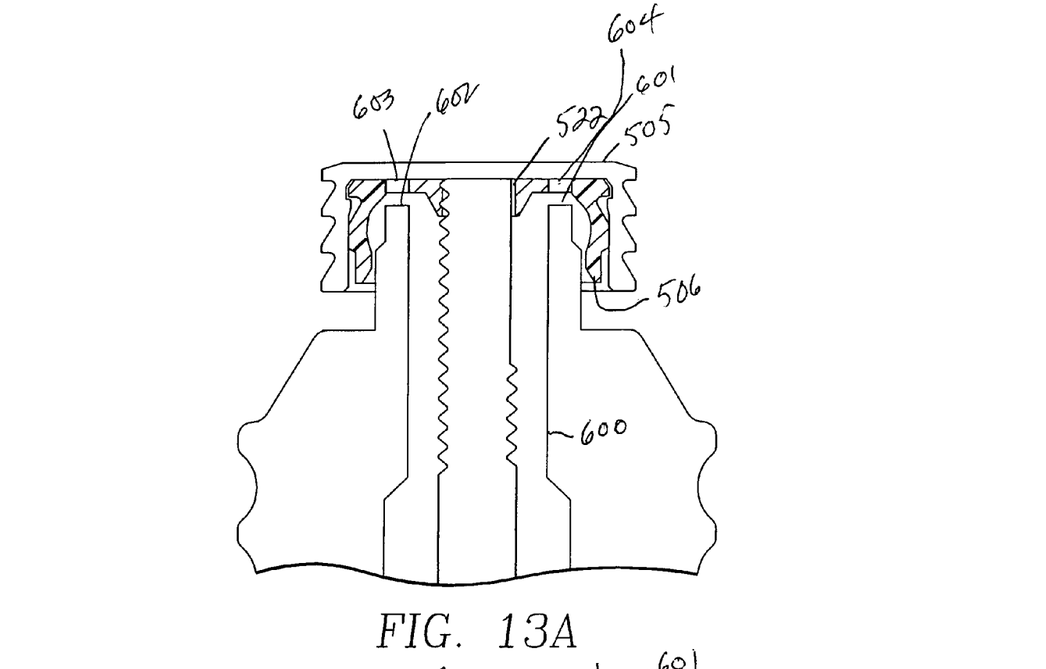
FIG. 13 shows a side elevation views in vertical cross section of a tool used to separate a cap from an insert when the cap is attached to the insert.
Figure 13B:
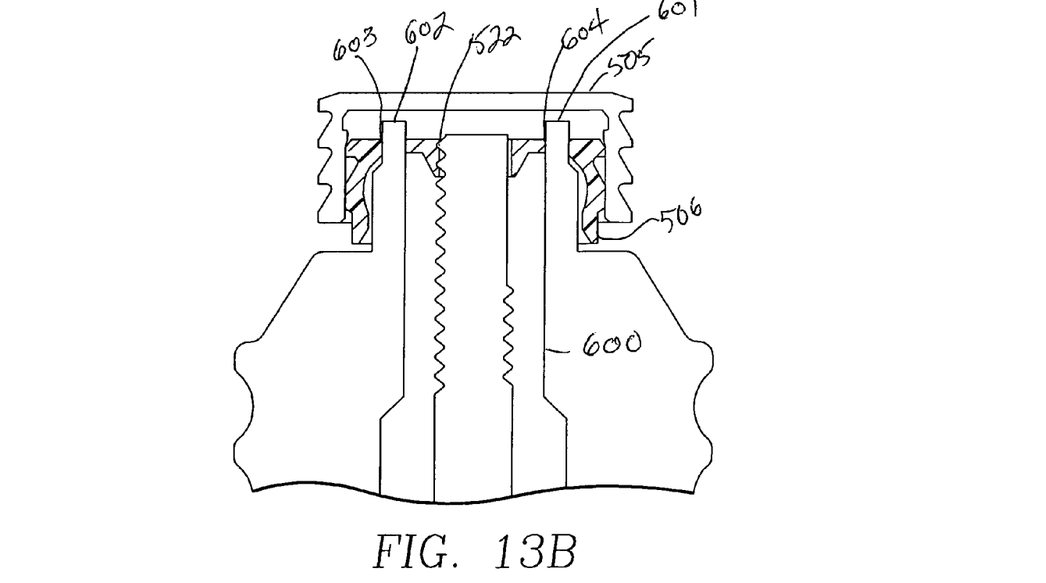
Figure 14:
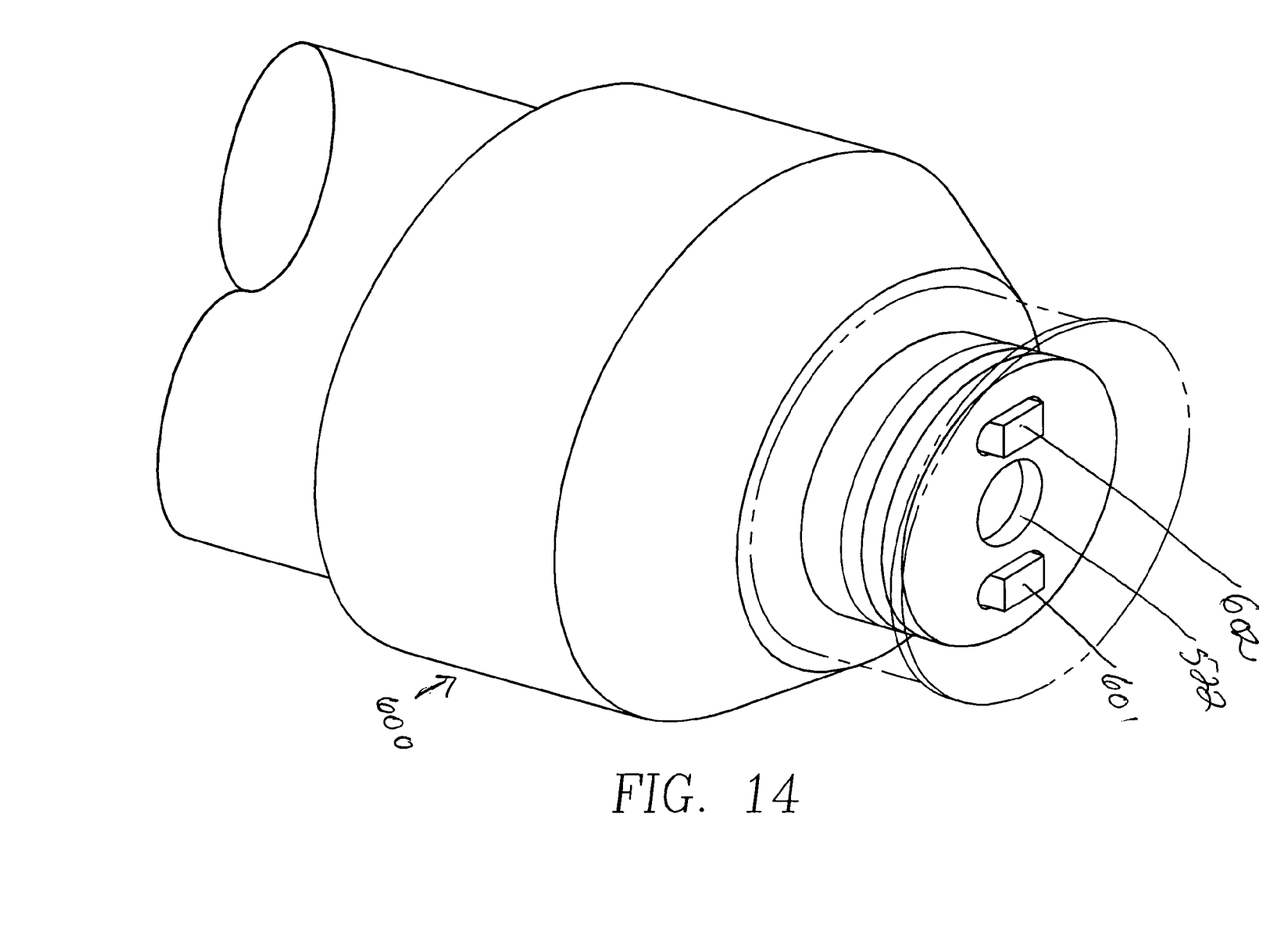
FIG. 14 shows the tool from FIG. 13 in perspective view.

See FIGS. 13 A/B and 14. A suitable rotatable tool 600 fits into opening 522 and, upon rotation of the tool, disconnects metal cap 505, as desired, from plastic insert 506. Projections 602 and 601 at the proximal end of tool 600 engage insert openings 603 and 604 alongside opening 522 to prevent rotation of the insert with respect to the cap.

An abutment member may have several different tissue cuff heights to match the surrounding gingival level. The minimum height for a non-hexed implant abutment will be of the order of 1.75 mm, while the minimum height for a hexed implant abutment will be around 2.75 mm, which will help in cases where the implant is at tissue level. This is lower than the height of all such attachments currently on the market today, and has the advantage of providing a much lower profile and increased patient comfort. Other heights will also be provided depending on the depth of the tissue. The low profile above the attachment is also better for tooth placement.

Abutments may be provided in a variety of different angles for accommodating different angular offsets, e.g., 10 to 20 degrees, in an implant. Such abutments may have a longitudinal axis at a predetermined angle to the direction of abutment attachment to an implant.

Although some preferred embodiments of the invention have been described above by way of example only, it will be understood by those skilled in the field that modifications may be made to the disclosed embodiment without departing form the scope of the invention, which is defined by the appended claims.

I claim:

1. A dental attachment assembly, comprising: an abutment for attachment to a dental implant, or to a bar, the abutment having an upper end that includes an inwardly-projecting socket, and an outer surface portion projecting downwardly from said upper end, said outer surface portion projecting above the tissue level in a patient's mouth when said abutment is secured in the implant or on the bar; and a two-part male member attached to said abutment, the first part of said two-part male member comprising a plastic insert having bottom and top surfaces, and an outwardly-flaring flange projecting from said insert top surface, a first skirt projecting from said flange, said first skirt having a cylindrical-shaped outer surface and a bottom edge for engagement with the upper end of said abutment, and, projecting from the center of the bottom surface of said insert, a retention member comprising a head for releasable snap engagement in said socket, said retention member being tiltable, rotatable and vertically movable in said socket, the second part of said two-part male member comprising a metal cap with a top, retentive features for attachment to a dental appliance, and a second skirt that includes a bottom projecting from the top of said metal cap, said metal cap having a size and shape for a firm snap fit over said first part with said first skirt projecting below the bottom of said second skirt.

2. The assembly as claimed in claim 1, wherein the retention member includes, at its distal end, a rounded flange with a flat or curved bottom surface of sufficient size and shape to pass through and seat below an inwardly-extending lip or flange in said socket to rotationally and vertically position said retention member in said socket.

3. The assembly as claimed in claim 1, wherein said outer surface of said abutment has a rounded portion projecting outwardly and downwardly from said upper end, providing a retentive undercut below the rounded projection, said outer surface tapering from said upper end, and terminating at a predetermined location above the tissue level when said abutment is secured in a patient's mouth.

4. The assembly as claimed in claim 1, wherein said inwardly projecting socket has, near its bottom end, internal wrench-engaging surfaces for engagement with an insertion tool for engaging said abutment with the implant or bar.

5. The assembly as claimed in claim 1, wherein said abutment has a head portion at said upper end, and a shaft depending downwardly from said head portion, wherein said shaft is at a predetermined angle to said head portion.

6. The attachment assembly of claim 1 wherein said outer surface of said abutment is rounded and an inner edge of the bottom edge at the distal end of said first skirt is inwardly beveled or rounded.

7. The assembly as claimed in claim 1, wherein said outer surface portion has an outward taper from said upper end and terminates at a predetermined location above the tissue level when said abutment is secured in a patient's mouth.

8. The assembly as claimed in claim 1, wherein said abutment has a head portion at the upper end, and a shaft depending downwardly from the head portion.

9. The assembly as claimed in claim 8, wherein said shaft is at a predetermined angle to said head portion.

10. The assembly as claimed in claim 1, wherein said abutment includes a head that has a flat lower endface for attachment to the bar.

11. A dental attachment assembly, comprising: a one-piece implant that includes, at its proximal end, an abutment portion, said abutment portion having an upper end, a socket projecting inwardly from said upper end, and an outer surface portion projecting downwardly from the upper end, the outer surface portion being positioned to project above tissue level when the implant is placed in a patient's mouth; a two-part male member attached to the abutment portion, the first part of said two-part male member comprising a plastic insert having a top surface, an outwardly-flaring first flange projecting from said insert top surface, a first skirt projecting from said first flange, said first skirt having a cylindrical-shaped outer surface, and, projecting from the bottom surface of said insert, a retention head for releasable snap engagement, and for tillable, rotatable and vertical movement in said socket; the second part of said two-part male member comprising a metal cap including a top and an upper end for engagement in a recess in a dental appliance, retentive features for attachment to a dental appliance, and a second skirt including a bottom and, projecting from the top of said metal cap, said metal cap having a size and shape for a firm snap fit over said first part with said first skirt projecting below the bottom of said second skirt.

12. The assembly as claimed in claim 11, wherein said outer surface of said abutment portion has a rounded portion projecting outwardly and downwardly from the upper end, providing a retentive undercut below the rounded projection, said outer surface portion tapering from said upper end, and terminating at a predetermined location above the tissue level when said implant is secured in a patient's mouth.

13. The attachment assembly of claim 1 or claim 11 wherein the top surface of said metal cap is flat.

14. The attachment assembly of claim 1 or claim 11 wherein the top surface of said plastic insert is flat.

15. The attachment assembly of claim 1 or claim 11 wherein the top surface of said metal cap and the top surface of said plastic insert are flat.

\* \* \* \* \*